United States Patent
Hicks

(10) Patent No.: US 7,841,985 B2
(45) Date of Patent: Nov. 30, 2010

(54) SENSOR IDENTIFICATION METHOD AND SYSTEM

(75) Inventor: Christopher Hicks, Boulder, CO (US)

(73) Assignee: Datex-Ohmeda, Inc., Louisville, CO (US)

( * ) Notice: Subject to any disclaimer, the term of this patent is extended or adjusted under 35 U.S.C. 154(b) by 989 days.

(21) Appl. No.: 11/645,246

(22) Filed: Dec. 22, 2006

(65) Prior Publication Data

US 2007/0208236 A1 Sep. 6, 2007

Related U.S. Application Data

(62) Division of application No. 10/355,440, filed on Jan. 31, 2003, now abandoned.

(60) Provisional application No. 60/353,471, filed on Jan. 31, 2002.

(51) Int. Cl.
 *A61B 5/05* (2006.01)
 *A61B 5/02* (2006.01)

(52) U.S. Cl. ............... 600/507; 600/322; 600/324; 600/334; 600/504

(58) Field of Classification Search ............. 600/504
 See application file for complete search history.

(56) References Cited

U.S. PATENT DOCUMENTS

| | | |
|---|---|---|
| 3,720,199 A | 3/1973 | Rishton et al. |
| 3,790,910 A | 2/1974 | McCormack |
| 4,258,251 A | 3/1981 | Donaldson |
| 4,303,984 A | 12/1981 | Houvig |
| 4,570,160 A | 2/1986 | Imazeki et al. |
| 4,621,643 A * | 11/1986 | New et al. .......... 600/331 |
| 4,684,245 A | 8/1987 | Goldring |
| 4,700,708 A | 10/1987 | New, Jr. et al. |
| 4,942,877 A | 7/1990 | Sakai et al. |
| 5,246,003 A | 9/1993 | DeLonzor |
| 5,259,381 A | 11/1993 | Cheung et al. |
| 5,429,129 A | 7/1995 | Lovejoy et al. |
| 5,503,148 A | 4/1996 | Pologe et al. |
| 5,645,059 A | 7/1997 | Fein et al. |
| 5,654,712 A | 8/1997 | Cheng |
| 5,722,403 A | 3/1998 | McGee et al. |
| 5,779,630 A | 7/1998 | Fein et al. |
| 5,818,985 A | 10/1998 | Merchant et al. |
| 5,830,129 A | 11/1998 | Baer et al. |
| 5,842,979 A | 12/1998 | Jarman |
| 5,891,024 A | 4/1999 | Jarman et al. |

(Continued)

*Primary Examiner*—Patricia C Mallari
(74) *Attorney, Agent, or Firm*—Marsh Fischmann & Breyfogle LLP

(57) ABSTRACT

An inventive method and system are provided for identifying a compatible photoplethysmographic sensor when interconnected to a given photoplethysmographic monitor. The method and system may further provide for the identification of which of a plurality of compatible sensors is interconnected to allow for selective calibration of the photoplethysmographic monitor. In this regard, the system and method may entail provision of a predetermined drive or test signal to a light source and/or identification element (i.e., sensor elements) of a photoplethysmographic sensor, and the obtainment of a corresponding output signal for use in sensor identification. In one approach, an output signal is obtained from at least one of three sensor elements each of which is interconnected between a different pair of sensor terminals which is a unique combination of two of four sensor terminals on the sensor. In this regard, individual circuits may be formed through each sensor element allowing for enhanced flexibility in signal application.

30 Claims, 5 Drawing Sheets

U.S. PATENT DOCUMENTS

| | | |
|---|---|---|
| 5,934,277 A | 8/1999 | Mortz |
| 5,987,343 A | 11/1999 | Kinast |
| 5,995,855 A * | 11/1999 | Kiani et al. ................. 600/310 |
| 6,351,658 B1 | 2/2002 | Middleman et al. |

* cited by examiner

SENSOR IDENTIFICATION METHOD AND SYSTEM

CROSS REFERENCE TO RELATED APPLICATIONS

This application is a divisional application of U.S. application Ser. No. 10/355,440 having a filing date of Jan. 31, 2003 now abandoned, which claimed priority under 35 U.S.C. 119(e)(1) to U.S. Provisional Application No. 60/353, 471 entitled: "Sensor Identification Method and System," filed on Jan. 31, 2002; the contents of which are incorporated herein as if set forth in full.

FIELD OF THE INVENTION

The present invention relates to the field of photoplethysmography, and more specifically, to an improved method and system for identifying a photoplethysmographic sensor selectively interconnectable to a photoplethysmographic monitor, e.g. to confirm compatibility with and/or otherwise "calibrate" the monitor for accurate measurements. The invention is particularly apt for pulse oximetry applications.

BACKGROUND OF THE INVENTION

In the field of photoplethysmography light corresponding with two or more different centered wavelengths may be employed to non-invasively determine various blood analyte concentrations. For example, blood oxygen saturation ($SpO_2$) levels of a patient's blood may be monitored in pulse oximetry systems by measuring the absorption of oxyhemoglobin and reduced hemoglobin using red and infrared light. The measured absorption data allows for the determination of the relative concentration of reduced hemoglobin and oxyhemoglobin, and therefore $SpO_2$ levels, since reduced hemoglobin absorbs more light than oxyhemoglobin in the red band and oxyhemoglobin absorbs more light than reduced hemoglobin in the infrared band; and since the absorption relationships of the two analytes in the red and infrared bands are known. See e.g., U.S. Pat. Nos. 5,934,277 and 5,842,979.

As may be appreciated, in order to accurately compute blood analyte concentrations, it is important for pulse oximetry systems to be preset, or "calibrated", in relation to the center wavelengths of red and infrared light employed. In this regard, pulse oximetry arrangements typically comprise a disposable or reusable sensor that is releasably attached to a given patient's appendage (e.g., finger, ear lobe, infant foot or nasal septum) for a given patient monitoring procedure. The sensor carries at least one red light source and one infrared light source, as well a light detector to provide an output signal indicative of the light received thereby (e.g. the red and infrared light passing through the patient appendage). In turn, the sensor may be connected or selectively interconnectable to a cable that is selectively interconnectable to a photoplethysmographic monitor to process the detector output signals.

Given such selective interconnections, a number of approaches have been developed for identifying a given sensor to an interconnected photoplethysmographic monitor so as to insure compatibility (e.g. so that the monitor may process the sensor detector output signal based upon assumed or calibrated values, or algorithms, reflective of the center wavelength(s) of the interconnected sensor light source(s)). Such known approaches largely entail the utilization of dedicated sensor componentry and corresponding cable connections, thereby adding cost, complexity and mass. Further, many of the known approaches raise reliability concerns since the identifying componentry can be easily implemented by sensor suppliers offering sensors that do not otherwise satisfy performance parameters established for accurate measurements by and/or effective use of a given interconnectable monitor.

SUMMARY OF THE INVENTION

A general objective of the present invention is to provide an improved approach for photoplethysmographic sensor identification.

A more specific objective of the present invention is to provide for photoplethysmographic sensor identification in a manner that does not require dedicated sensor componentry or increased complexity.

Yet a further objective of the present invention is to provide for improved photoplethysmographic sensor identification in a manner that facilitates enhanced reliability and/or otherwise allows for increased identification capabilities.

One or more of the above objectives and additional advantages are realized by the present invention which provides for the identification of compatible/incompatible photoplethysmographic sensors by a given photoplethysmographic monitor interconnected thereto. To realize such benefits, the present inventor has recognized that the light source(s) and/or light detector(s) employed in photoplethysmographic sensors have unique and predeterminable operating characteristics. Therefore, a predetermined drive, or interrogation test, signal can be provided to a given sensor interconnected to a given monitor to yield a "test signature" that can be used to identify the sensor, e.g. via comparison to one or more "reference signatures" pre-established in relation to one or more sensors known to be compatible with the monitor.

The inventive method and system entail: (i.) the provision of a predetermined drive signal to the light source(s) of a given photoplethysmographic sensor, (ii.) the obtainment of at least one of an output signal from a light detector comprising the sensor (e.g. which is indicative of light received thereby) and an output signal from the light source(s) and/or an associated identification element (e.g. which is indicative of any signal passing therethrough), and (iii) the utilization of the output signal to identify the photoplethysmographic sensor. As may be appreciated the predetermined drive signal and the output signal may be provided and processed, respectively, by a photoplethysmographic monitor to which a given photoplethysmographic sensor has been selectively interconnected. Such monitor may compare the test signature obtained via processing to one or more stored reference signatures that correspond with known compatible sensors.

Sensor "identification" confirms that a given sensor is compatible for use with an interconnected photoplethysmographic monitor. In turn, for example, the monitor may be enabled to make "photoplethysmographic measurements" utilizing the interconnected sensor. Alternatively, if compatibility is not confirmed, the monitor may be totally or partially disabled, e.g. to "lock-out" use of the sensor with the monitor for all or at least certain "photoplethysmographic measurement" functionalities. For purposes hereof, "photoplethysmographic measurements" may entail blood analyte determinations, including in particular blood oxygen saturation values, as well as pulse/heart rate, and other related determinations. In conjunction with sensor identification, the inventive method and system may provide for an identification of which of a plurality of compatible sensors is interconnected to a monitor. A sensor detector output signal may then be processed using stored selected/calibrated values, or algorithms, corresponding with the identified sensor, for photoplethysmographic measurements.

In one sensor identification approach, a sensor light detector output signal may be utilized to yield a test signature that simply indicates whether a light source(s) of an interconnected sensor emits light in response to a predetermined drive signal. Further, the test signature may indicate when such emission(s) is evidenced in the light detector output signal in response to the predetermined drive signal. In this regard, it should be appreciated that, for any given photoplethysmographic sensor, the illumination response of the corresponding light source(s) (e.g. the capability and/or time delay to emit light) and the output signal response of the corresponding light detector (e.g. the time delay and wavelength sensitivity for signal response) may be predetermined for a given predetermined drive signal, i.e. to establish a reference signature. In connection with this approach, the method may further provide for the use of a predetermined drive signal whose magnitude (e.g. voltage/current) is varied in a predetermined manner. This approach yields a test signature comprising one or more portions per source, wherein each portion indicates whether a given source was on or off during each of one or more corresponding time periods. In turn, the test signature portions may be compared to corresponding portions of one or more reference signature(s) of known compatible sensors for a given monitor.

To identify a compatible sensor(s) having a plurality of light sources, a corresponding reference signature(s) may be established which is indicative of whether two or more of the light sources emit light in response to corresponding portions of a predetermined drive signal (e.g. such portions applying the same or different signal magnitude levels to the sources). Such reference signature(s) may be stored at a given photoplethysmographic monitor and compared with a corresponding test signature obtained from a given interconnected sensor to be identified. As will be appreciated, the use of plural light sources for sensor identification provides added information to the test signature and reference signature(s), thereby enhancing the identification process.

In another sensor signature identification approach, a detector output signal may be utilized to yield a test signature that indicates the intensity of light emitted by the light source(s), as detected by the detector, of an interconnected sensor in response to a predetermined drive signal. Further, the test signature may indicate when such light intensity is evidenced by the light detector output signal in response to the predetermined drive signal. In conjunction with this approach, it should be appreciated that, for a given photoplethysmographic sensor, the light source(s) utilized therein will have a predeterminable, corresponding emission intensity-to-time function (e.g. for ramping up/down), and the light detector utilized therein will have a predeterminable output response (e.g. a time delay for and wavelength sensitivity of signal response), for a given predetermined drive signal. As such, the invention may provide for a determination of whether the light source(s) emits radiation and light detector detects radiation in accordance with one or more predetermined intensity-to-time functions established in relation to one or more known, compatible sensors. In that regard, this approach yields a test signature comprising one or more intensity indication portions per light source that may be compared to corresponding portions of one or more reference signature(s) of known compatible sensors stored by a given monitor. In connection with this approach, the method may again provide for the use of a predetermined drive signal whose magnitude (e.g. voltage/current) is varied in a predetermined manner.

When a photoplethysmographic sensor includes a plurality of light sources the detector output signal may be utilized to determine whether two or more of the light sources emit radiation within corresponding predetermined intensity ranges, as detected by the light detector, in response to the predetermined drive signal. Further determinations can also be made as to whether the two light sources emit radiation that is detected in accordance with corresponding, predetermined intensity-to-time functions.

In making the foregoing determinations regarding the intensity of light source emissions, at least one test signature value may be obtained in an identification procedure which is indicative of a ratio between a current applied to a sensor light source(s) and the measured detector output current. In turn, the test signature value(s) may be compared to pre-established reference signature values corresponding with like ratios for known, compatible sensors when a like drive signal is applied thereto. The utilization of "current ratios" may provide a number of advantages, e.g. cancellation of signal noise components.

In conjunction with the above-noted approaches it may be noted that, since a detector output signal is utilized for sensor identification, a sensor under test should be provided or otherwise oriented so that the light source(s) and light detector thereof are in at least partial alignment. Further, to facilitate sensor identification, either prior to or after positioning on a patient appendage, the invention may utilize preprogrammed functionality that utilizes a sensor detector output signal to automatically determine whether the interconnected sensor has been attached to a patient (e.g. via comparisons to predetermined thresholds), then utilizes corresponding predetermined reference signatures of known compatible sensors for identification. That is, different reference signature sets may be selected in relation to the determination of whether the sensor under test is attached or unattached to a patient.

In yet another sensor identification approach, an output signal from an interconnected sensor light source(s) (e.g. which is indicative with any signal passing therethrough) may be utilized to yield a test signature which indicates whether the light source(s) emits light in response to a predetermined drive signal, and if so, a magnitude of the output signal. In the later regard, it should be appreciated that, e.g. for any given photoplethysmographic sensor, the voltage drop across the corresponding light source(s) may be predetermined for a given predetermined drive signal, i.e. to establish a reference signature that may be compared to a test signature for identification.

In connection with this approach, the invention may further provide for the use of a predetermined drive signal whose magnitude (e.g. current/voltages) and/or polarity is varied in a predetermined manner. In the former regard, it should be appreciated that, e.g. for any given sensor the magnitude of voltage drop across the corresponding light source(s) has a predeterminable relationship to the magnitude of the current passing through the light source(s) and that such relationship may be non-linear. As such, distinct reference signatures may be established/utilized that comprise a plurality of portions corresponding with each light source (e.g. each portion corresponding to a different drive signal magnitude).

As to the variation of drive signal polarity, it may be appreciated that, for sensors utilizing a diode light source(s), the polarity of the predetermined drive signal determines the operability of the diode light source(s). That is, the drive signal may be selectively forward-biased and reverse biased, wherein the magnitude of the diode light source(s) output signal will be substantially zero when reverse-biased. Such biasing yields further test and reference signature information for sensor identification.

Of note, the utilization of a light source(s) output signal for sensor identification may be advantageous in that the light source(s) and detector of a sensor need not be aligned for sensor identification. As such, the identification procedure may be completed either prior to or after attachment to a patient.

To further enhance the accuracy and reliability of the various approaches noted above, the predetermined drive signal may be provided for a number of cycles to obtain a corresponding number of test signatures. For example, where a predetermined voltage is sequentially applied for n cycles to m source(s) comprising a given interconnected sensor, n test signatures may be obtained from the output signal, wherein each of the test signatures includes at least m signature portions. In turn, corresponding portions of the test signatures may be statistically processed to enhance the accuracy of identification. Such processing may entail the computation of average, median, range and/or standard deviation values that are employable in comparing and potentially matching test signatures to reference signatures. In that regard, it should also be noted that two or all of the various approaches noted above can be utilized in combination to further enhance the accuracy of sensor identification.

When the photoplethysmographic sensor to be identified includes a plurality of light sources (e.g. with a single detector), the predetermined drive signal utilized for sensor identification may provide for pulsing of such light sources in accordance with a predetermined multiplexing scheme. Further, the utilization of the detector output signal may entail demultiplexing of the signal in corresponding relation to the predetermined multiplexing scheme. The predetermined multiplexing/demultiplexing schemes may be any of several known in the art, including one selected from a group consisting of time division multiplexing, frequency division multiplexing and code division multiplexing. Any of these schemes facilitate the separate processing of detector output signal portions that correspond with the different light sources present in the sensor to be identified.

In yet a further aspect of the invention, the present invention may further provide for the conversion of an analog output signal from the detector and/or light source(s) into digital form for digital processing. Such conversion may preferably provide for data sampling at a rate which is at least two times greater than the greatest modulation frequency applied to the light source(s).

In an additional aspect, the invention may be employed to identify sensors having at least two light sources and a light detector, wherein when interconnected to a compatible monitor at least one of the light sources is only utilized for sensor identification purposes (e.g. such light source is not utilized for photoplethysmographic measurements).

By way of primary example, in certain current applications a photoplethysmographic sensor having three light sources and a detector is employable with two different types of photoplethysmographic monitors. When interconnected with a first type of photoplethysmographic monitor, first and second ones of the sensor light sources are utilized for photoplethysmographic measurements (e.g. a first infrared light source and a first red light source). When interconnected to a second type of photoplethysmographic monitor, first and third ones of the sensor light sources are employed for photoplethysmographic measurements (e.g. the first infrared light source and a second red light source).

The invention may be employed with either the first and/or second type of photoplethysmographic monitors. For example, when the sensor is interconnected to the first type of monitor the third light source will only be utilized by the monitor for sensor identification purposes. Such an arrangement advantageously makes use of the "extra" light source (e.g. not otherwise employed for photoplethysmographic measurements in one of the alternative applications) for sensor identification purposes.

According to a general series of embodiments, an inventive photoplethysmographic system includes a photoplethysmographic sensor having first and second light sources and an identification element (e.g. a third light source). These light sources and identification element are electrically interconnected between four terminals on the sensor. In this regard, each sensor element (e.g. each light source or identification element) is interconnected between a different pair of sensor terminals (i.e. each different pair of sensor terminals comprises a unique combination of two of the four sensor terminals). Stated another way, none of the sensor elements are in a parallel relationship with another sensor element and each pair of terminals shares at least one terminal with another sensor terminal pair.

The system also includes a photoplethysmographic monitor releasably interconnected to each of the first, second, and third sensor terminal pairs. For example, the monitor may be selectively interconnected to the sensor using a cable, wherein the cable itself may be connected or selectively interconnectable to the sensor. The monitor is operative to selectively apply predetermined signals to one of the terminals of each of the three sensor terminal pairs in order to obtain output signals at a second terminal of each of those pairs. More particularly, the monitor is operable to selectively apply drive and/or interrogation signals to each of the sensor elements. In turn, the monitor is operable to obtain an output signal(s) at a second terminal of one or more of the terminal pairs in response to the interrogation and/or drive signals. One or more of these output signals may be utilized by a processor operatively associated with the monitor to identify the sensor interconnected to the monitor. For example, the outputs signal(s) may be processed to produce one or more test signature(s) for comparison with one or more stored reference signature(s). As may be appreciated, if the output signal(s) and/or test signature(s) does not correspond to a value(s) associated with known sensors, the monitor may be disabled.

In typical arrangements the monitor may be operative to apply interrogation and/or drive signals of varying magnitudes and/or polarities to the sensor terminals. For example, drive signals may be provided to selectively pulse the light sources during photoplethysmographic monitoring. In turn, for monitoring purposes, the sensor will further include a light detector for providing an output signal indicative of the light from the light sources as attenuated by patient tissue.

While the monitor is operable to apply interrogation and/or drive signals across any of the sensor elements, in a given system arrangement the identification element will typically be utilized only to provide an output signal for identification purposes. In one embodiment, the identification element may comprise a diode. In this regard, the first and second light sources as well as the identification element may each comprise light emitting diodes. As may be appreciated, in typical applications the use of a simple diode identification element will yield an output signal that reflects a minimal and predeterminable voltage drop across the corresponding terminal pair in response to an applied interrogation signal. Accordingly, this voltage drop output signal may be utilized for sensor identification purposes.

In order to apply individual interrogation and/or drive signals to any of the sensor elements, the sensor terminals may be interconnected to the monitor via dedicated electrical pathways. In this regard, individual circuits may be formed through any of the sensor elements allowing the monitor to independently apply signals to a desired sensor element. Furthermore, these individual circuits allow for switching the polarity of an interrogation signal as applied to a given sensor element.

In a sensor identification approach applicable with the photoplethysmographic system utilizing the four-terminal, three-sensor element sensor configuration, one or more interrogation signals are applied across a pair of terminals associated with the identification element and/or light sources in order to obtain one or more output signal(s). In turn, the output signal(s) may be employed for sensor identification.

Applying a drive or interrogation signal across a given pair of terminals comprises applying a signal to a first terminal of the terminal pairs in order to obtain an output signal at the second terminal. In this regard, the signal applied to the first terminal may pass through the sensor element between the terminals. Accordingly, for a "known" sensor, the output signal at the second terminal may be predeterminably about the same or different from the input signal. For example, for a forward-biased, light emitting diode the output signal may reflect a minimal, yet predeterminable voltage drop relative to the input signal. On the other hand, for a reverse-biased, light emitting diode, the output signal may predeterminably indicate the absence of any signal passing through light emitting diode. Applying an interrogation signal to other types of identification element(s) (e.g. resistor(s)) may cause a predeterminable and relatively significant voltage drop and/or change in current between the first and second sensor terminals. In any case, the comparison of an output signal with a predetermined value may be utilized for sensor identification. As may be appreciated, in addition to applying an interrogation signal(s) to the identification element, one or more interrogation signals may be applied to the light sources to produce additional output signals. These additional output signals may be used separately or in combination with output signals from the identification element for sensor identification and/or monitor calibration purposes.

In one embodiment, an interrogation signal may be applied across the identification element and/or light sources in a manner that produces at least two output signals. In this regard, more accurate test signatures may be produced for sensor identification. Obtaining two output signals from a sensor element interconnected between a pair of terminals may require applying first and second interrogation signals or altering the polarity of a single interrogation signal as applied to the terminals.

In one embodiment, the magnitude of first and second interrogation signals, as applied to the identification element, is varied in order to produce two output signals. That is, the current level and/or voltage of the interrogation signal is varied between first and second signals in order to produce first and second output signals. For example, when the identification element is a light emitting diode, first and second interrogation signals having first and second current levels may be applied across the diode's sensor terminals. As may be appreciated, a voltage drop associated with each interrogation signal may be recorded as first and second output signals. The light emitting diode is selected such that first and second interrogation signals having first and second different current levels produce minimal and substantially equal voltage drops (i.e., output signals). In this regard, two predeterminable and substantially identical output signals may be produced in response to two different interrogation signals.

Once the output signals are utilized to identify the sensor, the photoplethysmographic monitor may be utilized to apply drive signals to the first and second light sources as well as a light detector in order to perform plethysmographic monitoring. In order to prevent crosstalk or other contamination from the identification element, which may be a light emitting diode, the circuit interconnected to the information element may be disabled prior to monitoring. In any case, the monitor is operable to provide drive signals to the light sources and detector in order to pulsate light through tissue-under-test as well as obtain an output signal indicative of that pulsating light as attenuated by said tissue.

Numerous additional aspects and advantages will be apparent to those skilled in the art upon review of the further description that follows.

DETAILED DESCRIPTION

FIGS. 1A, 2A and 1B, 2B illustrate two alternate photoplethysmographic system applications of the present invention. The illustrated systems may each identify and selectively employ compatible sensors, including sensors that are compatible with each of the systems. In the later regard, the invention is no way limited to dual compatibility implementations.

Figure 1A:
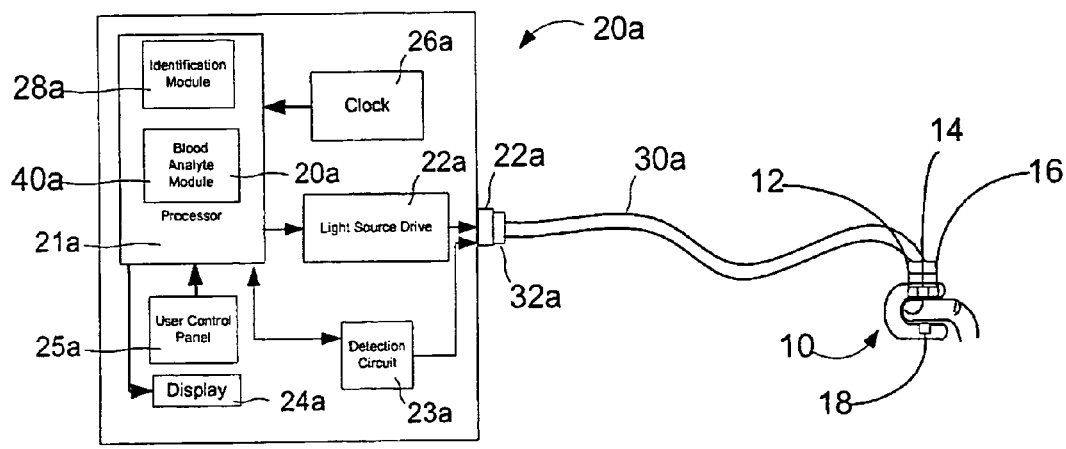
FIGS. 1A and 1B illustrate alternate embodiments of photoplethysmographic system applications of the present invention.
Figure 1B:
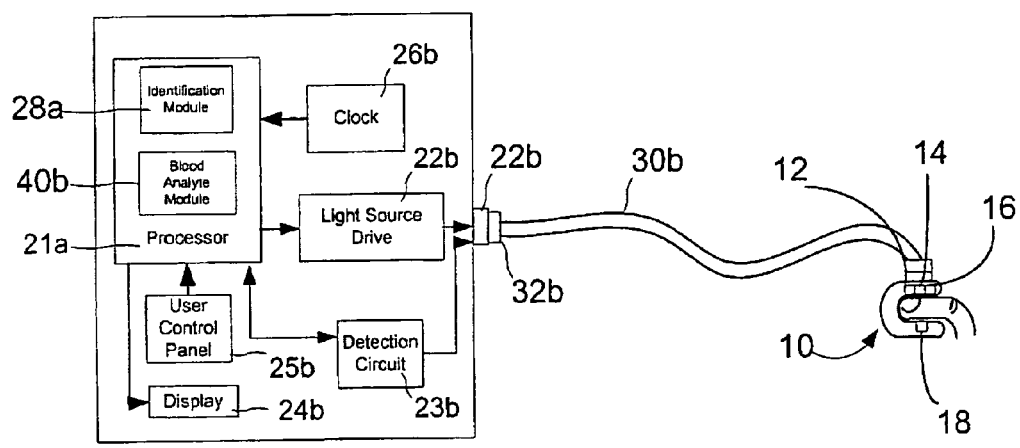

In the application of FIG. 1A, a first photoplethysmographic monitor 20a is shown interconnected to an interconnectable sensor 10 via a first type of cable 30a, while in the application of FIG. 1B a second photoplethysmographic monitor 20b is shown interconnected to the interconnectable sensor 10 by a second type of cable 30b. For purposes of the present description, sensor 10 is of a type that is compatible with either of the monitors 20a, 20b. The first and second photoplethysmographic monitors 20a, 20b may vary in type, however, including differing electrical configurations of their respective cable interconnection ports 22a, 22b and corresponding internal photoplethysmographic measurement features.

By way of example, monitor 20a may be designed with port 22a including two electrical pins or sockets for driving two light sources of a photoplethysmographic sensor. On the other hand, monitor 20b may be designed with port 22b including three electrical pins or sockets for driving two or more light sources of a photoplethysmographic sensor.

In the system applications shown in FIGS. 1A and 1B, photoplethysmographic monitors 20a, 20b comprise processors 21a, 21b and clocks 26a, 26b that may operate to trigger light source drives 22a, 22b to transmit drive signals via cables 30a, 30b to an interconnected sensor (e.g. the interconnectable sensor 10). More particularly, since sensor 10 is compatible in the illustrated applications, a drive signal may be provided in each application to pulse the light sources 12, 14 and/or 16 in accordance with a predetermined multiplexing scheme (e.g. a time-division, frequency-division or code-division multiplexing scheme) causing sources 12, 14 and/or 16 to emit light at different, corresponding centered-wavelengths for which monitors 20a, 20b have been preset or may be calibrated for operation.

By way of example, for normal photoplethysmographic measurements, in the system application of FIG. 1A light sources 12 and 14 may be selectively pulsed to illuminate a patient tissue under test (e.g. with red and infrared light at first and second centered wavelengths, respectively). In the system application of FIG. 1B light sources 12 and 16 may be selectively pulsed to illuminate a patient tissue under test (e.g. with red and infrared light at first and third centered wavelengths, respectively). Upon tissue illumination, a light detector 18 comprising sensor 10 may detect the intensity of light transmitted by the tissue under test and provide a corresponding output signal. In turn, monitors 20a, 20b may process the detector output signal utilizing stored values, or algorithms preset in relation to the center-wavelengths of the light sources 12, 14 and/or 16 of sensor 10. Of note, and as will be further described, the light sources 12, 14 and/or 16 are also employed in the illustrated applications for sensor identification purposes.

In the system applications of FIGS. 1A and 1B, the detector output signal of sensor 10 may be transmitted by cables 30a, 30b for conversion/conditioning by detection circuits 23a, 23b, and processing by processors 21a, 21b comprising monitors 20a, 20b, respectively. For example, detection circuits 23a, 23b may comprise amplification and analog-to-digital conversion componentry. If employed, the analog-to-digital componentry should preferably sample the detector signal at a rate which is at least two times the greatest frequency used for light source for multiplexing. Detection circuits 23a, 23b or processors 21a, 21b also may be provided to demultiplex detector signals (e.g. in corresponding relation to a given light source multiplexing scheme) so that signal portions corresponding with the light sources 12, 14 and/or 16 may be separately processed.

In conjunction with such processing, sensor 10 may be initially identified to confirm compatibility. Then, one or more photoplethysmographic measurements may be determined using the detector output signal and output to a user via monitor displays 24a, 24b. By way of example, the first and second photoplethysmographic monitors 20a, 20b may utilize the detector output signal to determine $SpO_2$ and pulse/heart rate values. Monitors 20a, 20b may each further include a user control panel 25a, 25b to allow for user control and override options as will be further described.

Figure 2A:
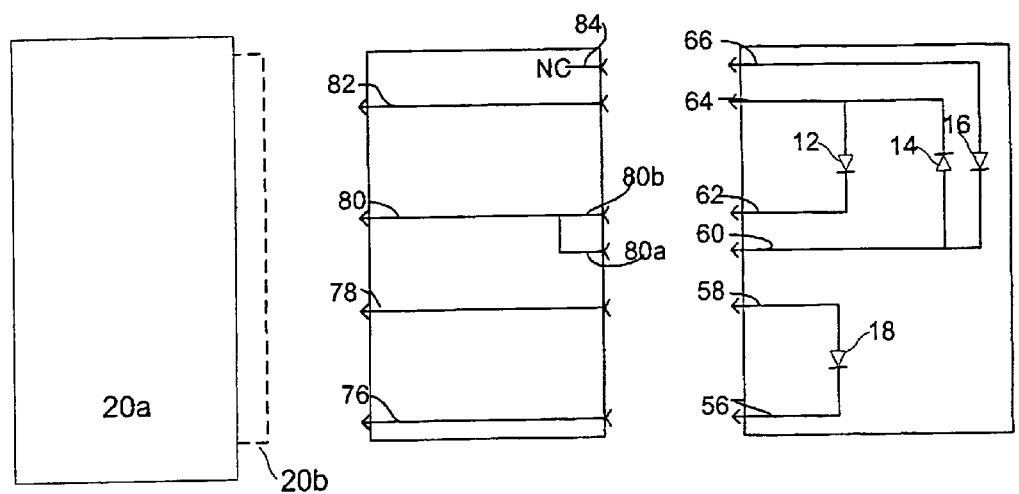
FIGS. 2A and 2B illustrate sensor, cable and monitor interconnections for the applications of FIGS. 1A and 1B.
Figure 2B:
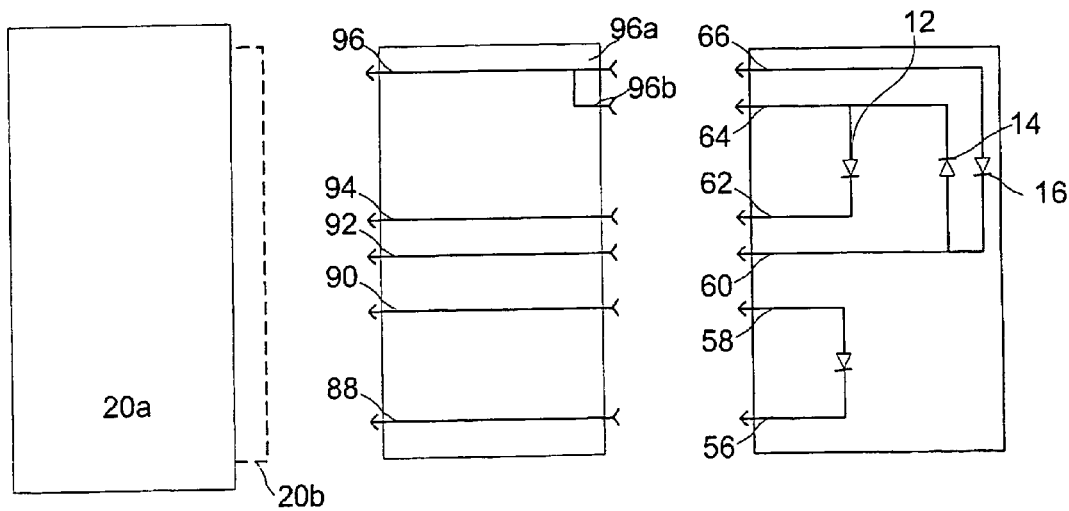

Referring now to FIGS. 2A and 2B, it can be seen that the light sources 12, 14 and 16 of sensor 10 may be electrically interconnected between sensor terminals 62 and 64, 60 and 64, and 60 and 66, respectively. In use of the FIG. 2A arrangement, either or both of light sources 12 and 14 may be utilized for identification purposes and photoplethysmographic measurements. For purposes of driving light source 12, clock 26a, processor 22a and drive source 26a of monitor 20a may cause a negative charge to be applied to sensor terminal 62 and a positive charge to be applied to sensor terminal 64 via cable connection lines 80 and 82, respectively. Selective driving of light source 14 may be provided by the selective application of a negative charge to sensor terminal 64 and positive charge to sensor terminal 60 via cable connection lines 82 and 80, respectively. As may be noted, the cable connection line 80 includes first and second spurs 80a and 80b for interconnection with sensor terminals 60 and 62, respectively, thereby facilitating an arrangement in which cable 30a presents a two terminal connection (i.e., via cable connection lines 80 and 82) to the port 22a of the first type of photoplethysmographic monitor 20a. To detect light signals transmitted by the tissue under test, processor 22a of monitor 20a may cause a negative charge to be applied to sensor terminal 56 while applying a positive charge to sensor terminal 58. As will be understood, such detection may be coordinated with the driving of light sources 12 and 14.

In use of the FIG. 2B arrangement, any or all of the light sources 12, 14 and 16 may be utilized for identification purposes, while only light sources 12 and 16 are utilized for photoplethysmographic measurements. For purposes of driving light source 12, clock 26b, processor 21b and drive source 22b of monitor 20b may cause a negative charge to be applied to sensor terminal 62 and a positive charge to sensor terminal 64 via cable connection lines 94 and 96, respectively. Light source 14 may be driven by applying a negative charge to sensor terminal 64 and a positive charge to terminal 60. Driving of light source 16 may be provided by application of a negative charge to sensor terminal 60 and a positive charge to sensor terminal 66 via cable connection lines 92 and 96, respectively. As may be noted, cable connection line 96 includes first and second spurs 96a and 96b for interconnection with sensor terminals 64 and 66, respectively, thereby facilitating an arrangement in which cable 20b presents a three terminal connection (e.g., via cable connection lines 92, 94 and 96) to the port 22b of monitor 20b. To detect light signals transmitted by the tissue under test, processor 22b of monitor 20b may cause a negative charge to be applied to sensor terminal 56 while applying a positive charge to sensor terminal 58. As will be understood, such detection may be coordinated with the driving of the light sources 12, 14 and/or 16.

Returning now to FIGS. 1A and 1B, processor unit 20a, 20b may comprise one or more data storage buffers to store detector output signal data values received from detector circuit 23a, 23b, as well as additional values computed by various computation modules comprising processor 20. In the latter regard, such computation modules may include a sensor identification module 40a, 40b for use in conjunction with the present invention, a blood analyte measurement module 28a, 28b for providing blood analyte information (e.g., blood oxygen saturation values), and other modules for providing other photoplethysmographic measurement information derivable from the data stored at the processor buffer(s).

In the later regard, blood analyte measurement module 28a, 28b may access buffer data values to compute differential absorption data sets (e.g., differential infrared light and differential red light data sets) from which blood analyte values may be determined utilizing stored values, or algorithms, which are based upon the center-wavelengths of the light sources of a given compatible sensor, e.g. light sources 12, 14, 16 of the interconnectable sensor 10. In this regard, blood analyte computation measurement modules 28a, 28b may incorporate known process functionalities, including those taught by U.S. Pat. Nos. 5,503,148; 5,842,979; 5,891,024 and 5,934,277.

As noted, sensor identification modules 40a, 40b, provide for the identification of compatible, interconnected sensors. More particularly, sensor identification module 40a, 40b may be provided to cause light source drives 22a, 22b to apply a predetermined drive signal, or interrogation test signal, to an interconnected sensor, and to process detector output signal data obtained from the interconnected sensor via detector circuit 23a, 23b to determine if the interconnected sensor is compatible.

In one identification approach, sensor identification modules 40a, 40b may process detector signal data to determine whether one or more light sources of an interconnected sensor (e.g. sensor 10) emit radiation in response to a interrogation test signal provided by light source drives 22a, 22b. More particularly, the detector signal data may be processed to determine whether a given interconnected sensor emits radiation within one or a plurality of different time periods in response to the drive signal. In this regard, the sensor identification modules 40a, 40b may utilize preset values, or algorithms, indicative of the illumination response(s) of light source(s) comprising one or more known, compatible sensor(s) when driven by a predetermined drive signal. That is, the "test signature" defined by the detector signal data may be compared with a "reference signature" defined by stored illumination response values or algorithms, to identify the interconnected sensor.

By way of example, in the system application corresponding with FIGS. 1B and 2B, light sources 12, 14 and 16 may be pulsed one or more cycles in accordance with a predetermined multiplexing scheme. In turn, the detector signal data may be demultiplexed to yield detector signal data portions in corresponding relation to the pulsing of sources 12, 14 and 16. Such portions may then be processed in relation to (e.g. compared to) stored values, or algorithms, pre-established in corresponding relation to the light sources of one or more known, compatible sensors, including sensor 10. In turn, stored look-up values or algorithms (e.g. based on the center-wavelengths of the sources in sensor 10 may be selected/calibrated for use in photoplethysmographic measurements.

In another identification approach, the sensor identification modules 40a, 40b may process the detector output signal data to determine whether one or more light sources of an interconnected sensor (e.g. sensor 10) emit light within a predetermined intensity range in response to a interrogation test signal provided by light source drives 22a, 22b. More particularly, the detector signal data may be processed to determine whether a given interconnected sensor emits light in accordance with at least one predetermined stored intensity-to-time function. In this regard, the sensor identification modules 40a, 40b may utilize preset values, or algorithms, indicative of the intensity-to-time function(s) corresponding with the light source(s) of one or more known, compatible sensor(s) when driven by a predetermined signal. Again, the "test signature" defined by the detector signal data may be compared with a "reference signature" defined by stored intensity-to-time function values, or algorithms, to identify the interconnected sensor.

By way of example, in the system application corresponding with FIGS. 1A and 1B, light sources 12 and 14 may be pulsed one or more cycles in accordance with a predetermined multiplexing scheme. In turn, the detector signal data may be demultiplexed to yield detector signal data portions in corresponding relation to the pulsing of sources 12 and 14. Such portions may then be processed in relation to (e.g. compared to) stored values or algorithms preset corresponding relation to the light sources of known, compatible sensors. Such processing confirms compatibility, and where the intensity-to-time attributes of plural known, compatible sensors are stored by monitors 40a, 40b, allows for the identification of a particular interconnected, compatible sensor, including sensor 10. Again, appropriate stored look-up values, or algorithms (e.g. based on the center-wavelengths of the light sources in sensor 10) may be selected/calibrated for use in photoplethysmographic measurements.

In yet another identification approach, the sensor identification modules 40a, 40b may process signal data obtained from output signals, or signals passing through, light sources 12, 14 and/or 16 in response to a interrogation test signal(s) applied thereto. For example, processing of such signal data may provide a "test signature" indicative of the voltage drop(s) across one or more of the light sources 12, 14 and/or 16 in response to a test interrogation signal comprising one or more magnitudes. Again comparison with corresponding "reference signatures" yields sensor identification. Utilization of interrogation signals as applied to one or more light sources will be more fully discussed below in relation to FIGS. 4 and 5.

Figure 3:
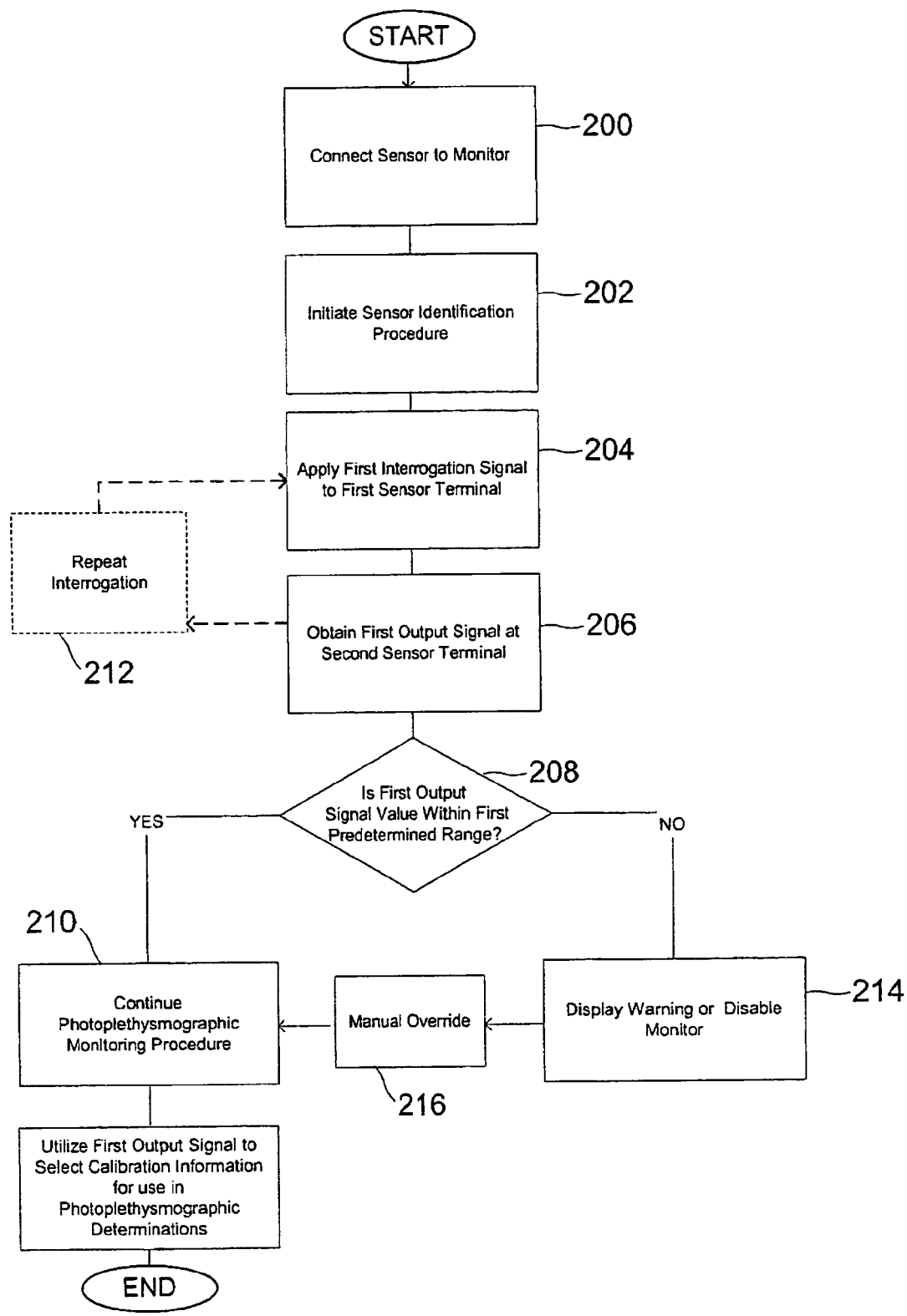
FIG. 3 illustrates an automated sensor identification procedure which implements the present invention.

As will be appreciated, automated sensor identification procedures may be readily implemented at monitors 20a, 20b. FIG. 3 illustrates such functionalities. As shown, set-up for the procedure entails the interconnection of a sensor (e.g. sensor 10) to a monitor 20a, 20b (step 200). In the applications of FIGS. 1A, 2A and 1B, 2B such interconnection requires the selective interconnection of connector end 32a, 32b of cable 30a, 30b to port 22a, 22b of photoplethysmographic monitor 20a, 20b, respectively, and the interconnection of a connector end 34a, 34b of cable 30a, 30b to sensor 10.

Following interconnection, the sensor identification procedure may be initiated (step 202). Such sensor identification procedure may be automatically initiated by monitor 20a, 20b upon electrical sensing of one or more of the interconnections made in step 200 above. Alternatively, the sensor identification procedure may be initiated by a user via interface with user control panel 25a, 25b of monitor 20a, 20b, e.g. upon prompting by display 24a, 24b of monitor 20a, 20b. In any case, monitor 20a, 20b may be pre-programmed so that the sensor identification procedure must be completed or manually overridden by a user before photoplethysmographic measurements can proceed.

Upon initiation of the sensor identification procedure, sensor identification module 40a, 40b may cause monitor 20a, 20b to automatically apply a interrogation test signal to the interconnected sensor (step 204) and correspondingly obtain a detector output signal from the sensor, such output defining a sensor "test signature". For example, the test signature may indicate whether one or more light sources comprising the interconnected sensor emitted light during one or more time periods within a cycle of the interrogation test signal and/or the intensity of any light emitted by one or more of the sources during such time periods. Optionally, additional "test signatures" may be obtained by repeating the interrogation test signal cycle.

Upon obtainment of the test signature(s), processor 21a, 21b of monitor 20a, 20b may determine whether the test signature(s) is within a predetermined range of a "reference signature" (step 208) thereby indicating that a known, compatible sensor (e.g. sensor 10) is interconnected to the monitor 20a, 20b. In the later regard, one or more "reference signatures" may be stored at module 40a or 40b in corresponding preset relation to the expected performance of one or more sensors known to be compatible with the corresponding monitor 20a or 20b. Where a plurality of sensors are compatible with monitor 20a or 20b, a corresponding plurality of stored reference signatures may be employed to identify the given interconnected sensor. If the sensor is identified, monitors 21a or 21b may automatically provide for continuation of photoplethysmographic monitoring procedure (step 210), wherein one or more blood analyte concentration levels are determined by and monitors 20a, 20b (step 200). Alternatively, processors 21a, 21b may provide for an output to a user (e.g. at display 24a, 24b) indicating that a compatible sensor (i.e., sensor 10) has been detected and prompt the user to provide an input at user control panel 25a to initiate photoplethysmographic measurements procedures. In conjunction therewith, the blood analyte measurement module 28a, 28b may utilize stored values, or algorithms, selected/calibrated in corresponding relation to the identified sensor, to make photoplethysmographic measurements the identification output value may be utilized to select appropriate calibration values for sensor 10 (step 210).

In the event that the test signature obtained at step 208 is outside of the predetermined range, processor 21a, 21b may be pre-programmed to disable monitor 20a, 20b from continuing to a photoplethysmographic measurement procedure (step 214). Such disablement may be accompanied by a corresponding output at display 24a, 24b indicating to the user that an inappropriate, or incompatible sensor has been interconnected to the monitor 20a, 20b. Alternatively, a warning signal may be output to a user at display 24a, 24b, whereupon processor 21a, 21b may be pre-programmed to allow a user to provide an override input at user control panel 25a, 25b to continue photoplethysmographic measurement procedures (step 216). In another approach, where the test signature obtained at step 208 is outside the predetermined range, processor 21a, 21b may be preprogrammed to only partially disable monitor 20a, 20b from completing a photoplethysmographic measurement procedure (step 214). For example, while certain performance-enhancing functionalities of processor 21a, 21b may be disabled, other base measurement functionalities would not be disabled.

Figure 4:
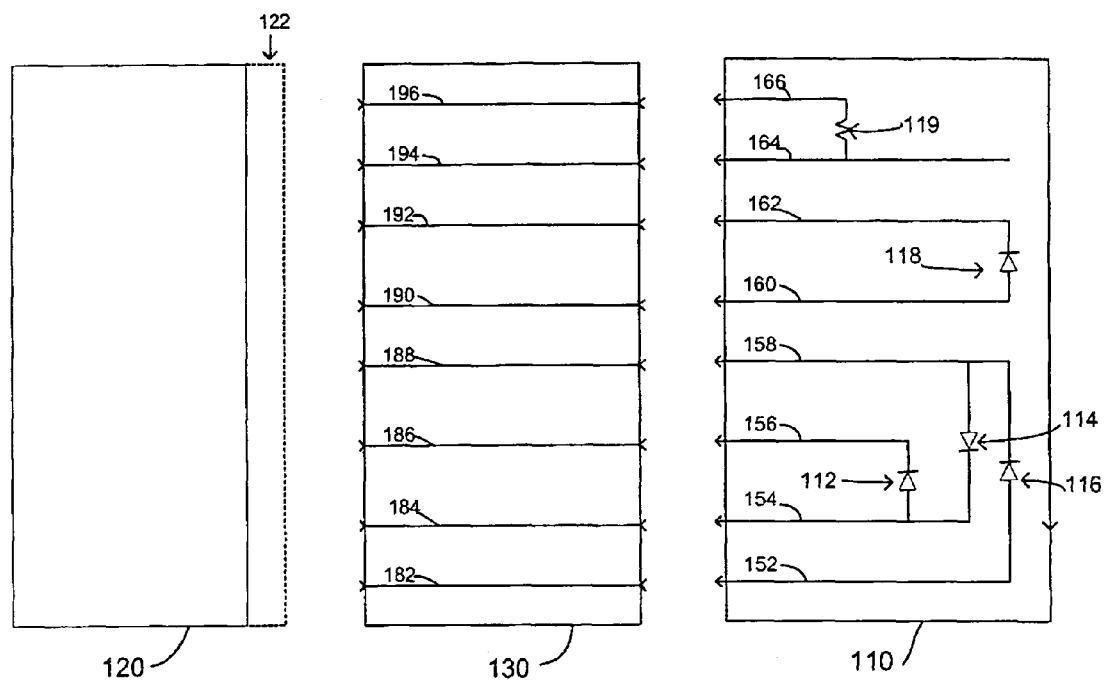
FIG. 4 illustrates a further embodiment of a sensor, cable and monitor.

Referring to FIG. 4, another embodiment of a photoplethysmographic system is provided that is operable to obtain output signals from one or more of light sources 112, 114, and 116 in response to interrogation signal(s) applied thereto. As with the systems described above in conjunction with FIGS. 1 and 2, the photoplethysmographic system includes a monitor 120 interconnected to a sensor 110 via a cable 130. The photoplethysmographic monitor 120 may include componentry similar or identical to photoplethysmographic monitors 20a and 20b as discussed above, including a clock, processor, sensor identification module, blood analyte measurement module, light source drives, etc. Likewise, the photoplethysmographic monitor 120 includes a port 122 having a plurality of electrical pins for interconnection to corresponding sensor terminals 152-166, located on the sensor 110.

As shown, the cable 130 utilizes eight lines, 182-196 to interconnect the sensor terminals 152-156 on the sensor 110 to the pins within the port 122. In this regard, each sensor terminal 152-156 on the sensor may be interconnected to the monitor 120 using a dedicated line 182-196. As may be appreciated, this allows for increased flexibility in applying drive and/or interrogation signals from the monitor 120 to the sensor elements (i.e. light sources, detectors, etc.) within the sensor 110.

The sensor 110 of FIG. 4 includes three light sources 112, 114, and 116 each interconnected between two of the four sensor terminals 152-158. In particular, light sources 112, 114, and 116 are each connected between a unique pair of sensor terminals 152-158. More particularly, each pair is a unique combination of two of the four sensor terminals 152-158, wherein each unique pair of terminals includes at least one terminal included in another pair of terminals. In particular, light source 112 is interconnected between sensor terminals 154 and 156; light source 114 is interconnected between terminals 158 and 154; and light source 116 is interconnected between sensor terminals 152 and 158. The sensor further includes, a detector 118 interconnected between sensors 160 and 162 and a bin resister 119 interconnected between sensor terminals 164 and 166.

Interconnection of the light sources 112, 114, and 116 between the four sensor terminals 152-156 allows interconnecting the light sources 112, 114 and 116 to the monitor using four dedicated lines 182-188. This four-terminal, three-light source arrangement allows for establishing a unique circuit through each light source 112, 114 and 116. For example, the monitor 120 may apply a positive charge to sensor terminal 152 and a negative terminal charge to sensor terminal 158 via cable lines 182 and 188, respectively, to apply a first drive or interrogation signal to light source 116. Accordingly, a corresponding output signal may be produced across terminals 152 and 158. Depending upon the electrical components included between each pair of sensor terminals 152-158, the polarity of the signal may be reversed as applied to each pair of sensor terminals. Accordingly, a signal may be applied with two polarities to produce two output signals. By way of example, light source 116, which is reversed biased in one direction, may produce separate outputs to a signal applied with two polarities. In this regard, if light source 116 is an LED, it may produce a minimal and predeterminable voltage drop across terminals 152 and 158 in response to a signal having a first polarity. Likewise, light source 116 may produce an open circuit output signal in response to the same signal applied having a second polarity. What is important is that each light source 112, 114, and 116 may receive one or more drive and/or interrogation signals from the monitor 120 allowing each light source 112, 114 and 116 to be utilized for identification purposes and/or photoplethysmographic measurements. However, in the embodiment described herein below, one of the light sources 112, 114 and 116 is used only for identification purposes.

Figure 5:
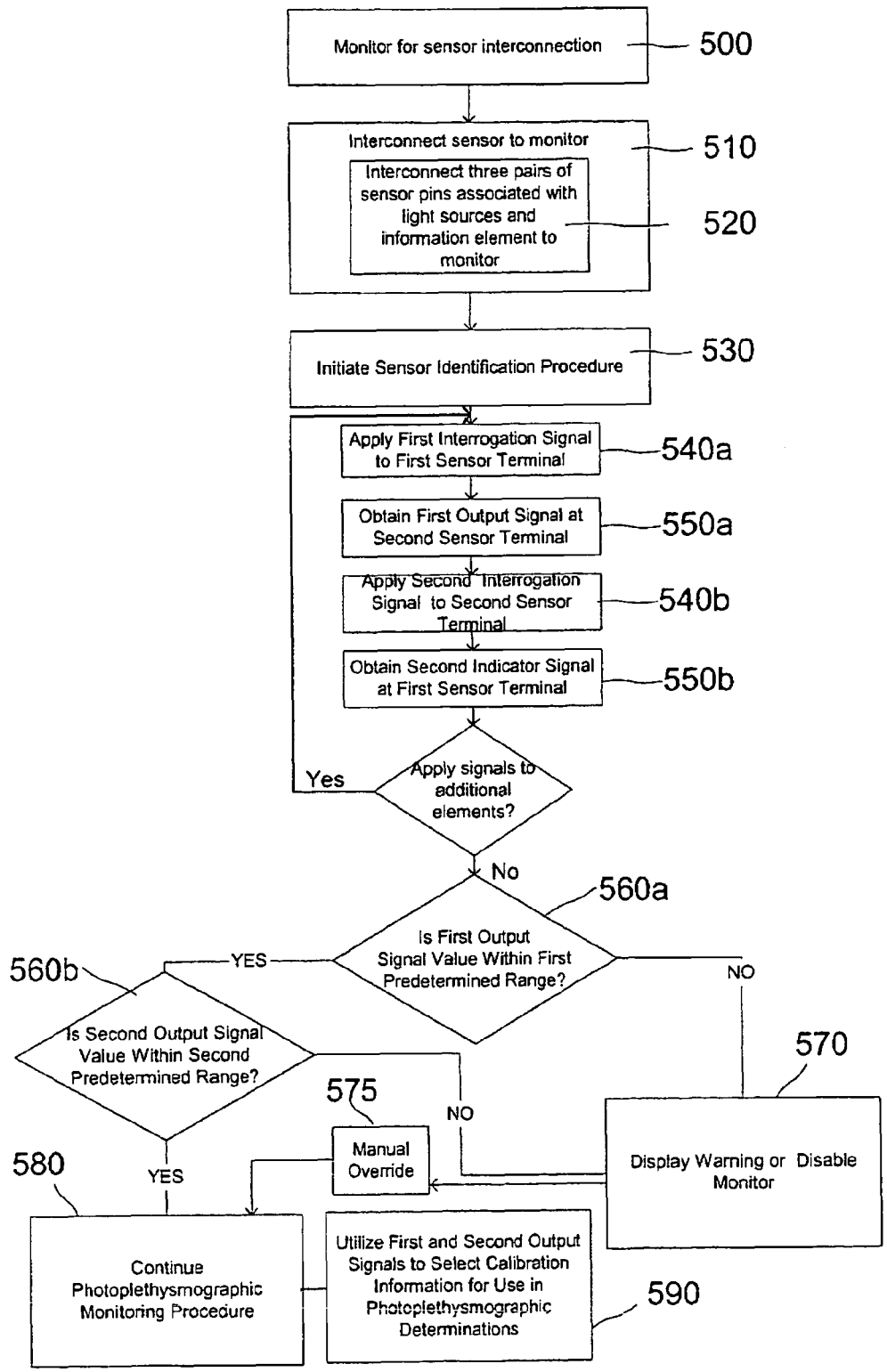
FIG. 5 illustrates an automated sensor identification procedure utilized with the system of FIG. 4.

FIG. 5 illustrates a sensor identification process that may be implemented with the photoplethysmographic system of FIG. 4. Initially the photoplethysmographic monitor 120 monitors (step 500) a first circuit to identify a continuity that indicates sensor connection. That is, photoplethysmographic monitor 120 continually monitors an initially open circuit through lines 194, 196 of cable 130. Upon interconnection (step 510) of the sensor 110 to the cable 130, which is interconnected to the photoplethysmographic monitor 120, bin resistor 119 is identified as being present across sensor terminals 164, 166. The bin resistor 119 completes the monitored circuit through lines 194 and 196 providing a continuity that indicates a sensor 110 has been interconnected (step 510) to the photoplethysmographic monitor 120. As may be appreciated, this bin resister may also, in some instances, be utilized to provide an output signal (e.g., a predeterminable voltage drop) in response to the monitoring signal. Accordingly this output signal may be utilized for obtaining sensor information and/or for identification purposes.

In conjunction with completing the monitored circuit through sensor terminals 164 and 166, interconnection (step 510) of the sensor 110 to the cable 130 also connects (step 520) a plurality of terminal pairs 152-158; 154-158; 154-156 and 160-162 associated with sensor elements 116, 114, 112 and 118 to the monitor 120. That is, in addition to the circuit formed through the bin resistor 119, four individual circuits are established using lines 182-192 of the cable 130. Each of those circuits may receive drive and/or interrogation signals from said photoplethysmographic monitor 120 for application across their respective sensor elements.

In response to the sensor 110 being interconnected (step 510) to the monitor 120, a sensor identification procedure may be initiated (step 530). In this regard, the monitor 120 may perform and open and short test through the terminal pairs 152-158; 154-158; 154-156 and 160-162 to determine whether sensor elements are present. If one of the circuits is open, the monitor may be disabled. Typically, the monitor 120 will utilize one of the three light sources 112, 114, and 116 to perform a sensor identification procedure (step 530).

For the discussion herein, it will be assumed that light source 116 is utilized for identification purposes, and light sources 112 and 114 are utilized for photoplethysmographic monitoring purposes. However, it will be appreciated that other combinations may be utilized. In order to utilize light source 116 as an identification element, the monitor 120 may selectively apply (steps 540a and 540b) one or more interrogation signals to one of the terminals 152, 158 of light source 116 in order to produce one or more output signals (steps 550a and 550b) at the other terminal for use in sensor identification. In this regard, the monitor 120 may apply a positive charge to sensor terminal 152 and a negative terminal charge to sensor terminal 158 via cable connection lines 182 and 188, respectively. Accordingly, passing the interrogation signal through the light source 116 may cause a predeterminable change to the signal (i.e., an output signal) that may be measured across sensor terminals 152, 158.

By way of example, passing a first interrogation signal through the light source 116 may result in a predeterminable minimal voltage drop (e.g., not greater than an a known threshold value) across terminals 152 and 158. Accordingly, this known response may be used for identification purposes. Alternatively, if a resistor were also be incorporated between terminals 152 and 158 (e.g., in series with light source 116; not shown) a predeterminable voltage drop having at least a minimum value may be produced across the terminals 152 and 158.

It will be noted that multiple interrogation signals may be applied across sensor terminals 152 and 158 for application to light source 116. In this regard, interrogation signals having different magnitudes (i.e. voltage and/or current levels) may be applied (step 540) across terminals 152 and 158 to obtain a plurality of outputs (step 550) for use in sensor identification. Furthermore, in some instances, interrogation signals may be applied (step 540) to one or both of the other light sources 112, 114 to obtain (step 550) additional outputs.

In a preferred embodiment, at least two interrogation signals having different magnitudes are applied (step 540) to terminals 152 and 158 to obtain (step 550) at least two output signals. Accordingly, these output signals are utilized by the monitor 120 (e.g. an identification module within the monitor) to identify the sensor 110 interconnected to the monitor 120. That is, these output signals will be compared (step 560) either individually or together to stored look-up values, or, processed to produce test signatures that will be compared (step 560) to stored look-up values. If the output signals/test signatures are within a predetermined range of the stored look-up values, the sensor 110 is determined to be compatible with the monitor 120 (i.e., the sensor is identified) and the photoplethysmographic monitoring procedure continues (Step 580). Once the sensor 110 is identified, the circuit through terminals 152 and 158 and identification element 116 may be deactivated from further use. That is, to prevent interference during monitoring, light source 116 may be deactivated. In this regard, the identification procedure may be performed at a first time and photoplethysmographic monitoring may be performed at a second subsequent time.

If the output value(s) are outside a predetermined allowable range, the monitor 120 may be disabled or display a warning to a user (step 570). However, in one embodiment a manual override may be provided (step 575) allowing a user to provide an override input at a user control panel, which may allow the monitor 120 to continue the photoplethysmographic monitoring procedure (step 580).

Once the monitor 120 identifies the sensor 110, the output signals/test signature and/or sensor identification may be utilized to access stored values, or algorithms. That is, the monitor 120 may select (step 590) appropriate calibration information for use with the sensor 110. Once properly calibrated, the monitor 120 may apply appropriate drive signals via sensor terminals 154-156 and 154-158, to pulse light sources 112 and 114, respectively. In conjunction with providing such drive signals to selectively pulse light sources 112 and 114, the monitor will also provide drive signals to the detector 118 via terminals 160 and 162. As in the embodiments described above, the detector 118 provides an output signal related to the light output of the pulsing light sources 112 and 114 as may be attenuated by patient tissue-under-test. Accordingly, the output of the detector 118 may be utilized to determine blood analyte values, such as SPO2, as well as physiological parameters such as heart rate and/or respiration rates.

The embodiments described above are for exemplary purposes only and is not intended to limit the scope of the present invention. Various adaptations, modifications and extensions of the described sensor/system/method will be apparent to those skilled in the art and are intended to be within the scope of the invention as defined by the claims which follow. By way of example, different light sources 112, 114 and 116 may be utilized for identification purposes by different photoplethysmographic monitors. In this regard, it will be appreciated that sensor 110 may be configured for use with multiple photoplethysmographic monitors. Accordingly, different ones of these monitors may utilize different combinations of light sources 112, 114 and 116 for identification and/or monitoring purposes.

What is claimed is:

1. A method using a photoplethysmographic system, comprising:
    releasably interconnecting four terminals of a photoplethysmographic sensor to a photoplethysmographic monitor,
    wherein a first pair of said four terminals on said sensor is connected for receiving first drive signals from said monitor for illuminating a first light source coupled between said first pair of terminals,
    wherein a second pair of said four terminals on said sensor is connected for receiving second drive signals from said monitor for illuminating a second light source coupled between said second pair of terminals,
    wherein a third pair of said four terminals on said sensor is connected for receiving an interrogation signal from said monitor for application across an identification element coupled between said third pair of terminals; and
    wherein said first, second, and third pairs of terminals each utilize a unique combination of said four terminals and wherein each said first, second, and third pairs of terminals share at least one terminal with another of said first, second, and third pairs of terminals;
    applying a first interrogation signal to a terminal shared by two of said pairs of terminals to obtain a first output signal across one of said two pairs of terminals;
    applying a second interrogation signal across the other of said two pairs of terminals to obtain a second output signal at said shared terminal; and
    utilizing at least one of said first and second output signals to identify said sensor.

2. The method of claim 1, wherein at least one of said applying steps comprise applying an electrical signal to one terminal of said third pair of terminals to obtain at least one output signal across said third pair of terminals.

3. The method of claim 2, wherein said identification element is a diode.

4. The method of claim 3, wherein said output comprises a minimal and predeterminable voltage drop across said diode.

5. The method of claim 3, wherein said applying step further comprises;
applying a first electrical signal to obtain a first output signal from said diode; and
applying a second electrical signal to obtain a second output signal from said diode.

6. The method of claim 5, wherein said first and second electrical signals have different magnitudes.

7. The method of claim 6, wherein said first and second electrical signals have first and second current levels.

8. The method of claim 7, wherein said first and second current level are selected to produce first and second minimal and predeterminable voltage drops across said diode.

9. The method of claim 8, wherein said first and second voltage drops are substantially equal.

10. The method of claim 7, wherein said first and second electrical signals have a positive polarity and a negative polarity, respectively, as applied to said identification element.

11. The method of claim 1, further comprising:
upon obtaining at least one of said first and second output signals, disabling said third pair of terminals on said sensor.

12. The method of claim 1, further comprising:
applying an interrogation signal across at least one of said first and second pairs of terminals to obtain an additional output signal from at least one of said first and second light sources.

13. The method of claim 1, further comprising:
establishing a connection with a fourth pair terminals on said sensor operable to complete a circuit monitored by said monitor to identify sensor interconnection.

14. The method of claim 13, further comprising:
applying an electrical signal to one terminal of said fourth pair of terminals to obtain an interconnection output signal at the other terminal of said fourth pair of terminals.

15. The method of claim 14, further comprising:
upon identifying said interconnection output signal, performing said applying steps.

16. The method of claim 14, wherein said interconnection output signal is utilized procure sensor information.

17. The method of claim 1, upon identifying said sensor, further comprising the step of:
applying predetermined drive signals to one terminal of at least one of said first and second terminal pairs on said sensor for controllably illuminating at least one of said first and second light sources.

18. The method of claim 17, wherein said at least one of said first and second light sources illuminates patient tissue-under-test.

19. The method of claim 18, further comprising:
establishing a connection with a fifth pair of terminals on said sensor having a light detector coupled there between; and
applying a detector drive signal to one terminal of said fifth pair of terminals to obtain a detector output signal at the other terminal of said third pair of terminals, wherein said detector output signal is indicative of light absorption of said tissue-under-test.

20. The method of claim 15, wherein said detector output signal is utilized for at least one of:
determining a blood analyte concentration value; and
determining at least one physiological parameter.

21. The method of claim 20, wherein said blood analyte concentration value comprises a blood oxygen value.

22. The method of claim 20, wherein said physiological parameter comprises a heart rate.

23. The method of claim 1, wherein releasably interconnecting further comprises:
interconnecting each terminal on said sensor to said monitor via a dedicated electrical pathway.

24. The method of claim 23, wherein four dedicated electrical pathways interconnect said first, second and third pairs of terminals on said sensor to said monitor.

25. The method of claim 1, further comprising:
comparing at least one of said first and second output signals to a predetermined range of values to select information for use in calibrating said monitor.

26. The method of claim 25, wherein when said at least one output signal is outside said predetermined range, said method further comprising at least one of:
providing an output to a user indicating that the sensor is not compatible with said monitor; and
disabling said monitor for use with said interconnected sensor.

27. The method of claim 25, wherein when said at least one output signal is within said predetermined range, said method further comprising:
utilizing said output signal to select one of a plurality of calibration values for use in photoplethysmographic monitoring.

28. A method using a photoplethysmographic system, comprising:
releasably interconnecting a photoplethysmographic sensor to a photoplethysmographic monitor,
wherein a first pair of terminals on said sensor is connected for receiving first drive signals from said monitor for illuminating a first light source coupled between said first pair of terminals,
wherein a second pair of terminals on said sensor is connected for receiving second drive signals from said monitor for illuminating a second light source coupled between said second pair of terminals,
wherein a third pair of terminals on said sensor is connected for receiving an interrogation signal from said monitor for application across a diode coupled between said third pair of terminals, wherein said diode forms an identification element; and
wherein said first, second, and third pairs of terminals each utilize a unique combination of terminals and wherein each said first, second, and third pairs of terminals share at least one terminal with another of said first, second, and third pairs of terminals;
applying a first electrical interrogation signal to a terminal shared by two of said pairs of terminals to obtain a first output signal across one of said two pairs of terminals;
applying a second electrical interrogation signal across the other of said two pairs of terminals to obtain a second output signal at said shared terminal, wherein at least one of said first and second applying steps comprises applying an electrical signal across said third pair of terminals, wherein at least one of said first and second outputs is an output across said third pair of terminals; and utilizing at least one of said first and second output signals to identify said sensor.

29. A method using a photoplethysmographic system, comprising:

releasably interconnecting a photoplethysmographic sensor to a photoplethysmographic monitor, wherein a first pair of terminals on said sensor is connected for receiving first drive signals from said monitor for illuminating a first light source coupled between said first pair of terminals, wherein a second pair of terminals on said sensor is connected for receiving second drive signals from said monitor for illuminating a second light source coupled between said second pair of terminals, wherein a third pair of terminals on said sensor is connected for receiving an interrogation signal from said monitor for application across an identification element coupled between said third pair of terminals; and wherein said first, second, and third pairs of terminals each utilize a unique combination of terminals and wherein each said first, second, and third pairs of terminals share at least one terminal with another of said first, second, and third pairs of terminals;

applying a first interrogation signal to a terminal shared by two of said pairs of terminals to obtain a first output signal across one of said two pairs of terminals;

applying a second interrogation signal across the other of said two pairs of terminals to obtain a second output signal at said shared terminal;

utilizing at least one of said first and second output signals to identify said sensor; and disabling said third pair of terminals on said sensor.

30. A method using a photoplethysmographic system, comprising:

releasably interconnecting a photoplethysmographic sensor to a photoplethysmographic monitor, wherein a first pair of terminals on said sensor is connected for receiving first drive signals from said monitor for illuminating a first light source coupled between said first pair of terminals, wherein a second pair of terminals on said sensor is connected for receiving second drive signals from said monitor for illuminating a second light source coupled between said second pair of terminals, wherein a third pair of terminals on said sensor is connected for receiving an interrogation signal from said monitor for application across an identification element coupled between said third pair of terminals; and wherein said first, second, and third pairs of terminals each utilize a unique combination of terminals and wherein each said first, second, and third pairs of terminals share at least one terminal with another of said first, second, and third pairs of terminals;

applying a first interrogation signal to a terminal shared by two of said pairs of terminals to obtain a first output signal across one of said two pairs of terminals;

applying a second interrogation signal across the other of said two pairs of terminals to obtain a second output signal at said shared terminal;

applying a third interrogation signal across at least one of said first and second pairs of terminals to obtain a third output signal from at least one of said first and second light sources; and utilizing at least one of said first, second and third output signals to identify said sensor.

* * * * *